(12) United States Patent
Peng et al.

(10) Patent No.: US 6,869,545 B2
(45) Date of Patent: Mar. 22, 2005

(54) COLLOIDAL NANOCRYSTALS WITH HIGH PHOTOLUMINESCENCE QUANTUM YIELDS AND METHODS OF PREPARING THE SAME

(75) Inventors: Xiaogang Peng, Fayetteville, AR (US); Lianhua Qu, Decatur, GA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 10/209,312

(22) Filed: Jul. 30, 2002

(65) Prior Publication Data

US 2003/0173541 A1 Sep. 18, 2003

Related U.S. Application Data

(60) Provisional application No. 60/308,727, filed on Jul. 30, 2001.

(51) Int. Cl.⁷ .............................................. C09K 11/00
(52) U.S. Cl. ............................... 252/301.6 S; 423/509; 423/566.1; 252/301.4 R; 252/301.4 S; 252/301.6 R
(58) Field of Search .................. 252/301.4 R, 301.4 S, 252/301.6 R; 423/509, 566.1

(56) References Cited

U.S. PATENT DOCUMENTS

| | | | |
|---|---|---|---|
| 5,260,957 A | * 11/1993 | Hakimi et al. ................ | 372/39 |
| 5,575,940 A | 11/1996 | Lofftus | |
| 6,207,229 B1 | 3/2001 | Bawendi et al. | |
| 6,326,144 B1 | * 12/2001 | Bawendi et al. ............... | 435/6 |
| 6,576,291 B2 | 6/2003 | Bawendi et al. | |
| 6,607,829 B1 | * 8/2003 | Bawendi et al. ............ | 428/403 |
| 6,617,583 B1 | * 9/2003 | Bawendi et al. ....... | 250/370.01 |
| 2002/0066401 A1 | * 6/2002 | Peng et al. ................... | 117/68 |
| 2002/0071952 A1 | 6/2002 | Bawendi et al. | |

OTHER PUBLICATIONS

Rotman, David, "Quantum Dot Com," *Technology Review*, Jan./Feb. 2000, pp. 51–57.

Wang, Y. Andrew et al., "Stabilization of Inorganic Nanocrystals by Organic Dendrons," *J. Am. Chem Soc.*, vol. 124, No. 10, 2002, pp. 2293–2298.

Brust, Mathias et al., "Synthesis of Thiol–derivatised Gold Nanoparticles in a Two–phase Liquid–Liquid System," *J. Chem. Soc. Chem. Commun.*, 1994, pp. 801–802.

Alivisatos, A.P., "Semiconductor Clusters, Nanocrystals, and Quantum Dots." *Science*, vol. 271, Feb. 16, 1996, pp. 933–937.

Alivisatos, A.P., et al., "Organization of 'nanocrystal molecules' using DNA," *Nature*, vol. 382, Aug. 15, 1996, pp. 609–611.

Peng, Xiaogang, et al., "Synthesis and Isolation of a Homodimer of Cadmium Selenide Nanocrystals," *AAngew. Chem. Int. Ed.*, vol. 36, 1997, pp. 145–147.

Weiss, Peter, "Connect the Dots: Transforming sunlight into electricity by means of quantum dust," *Science News*, vol. 157, Jun. 17, 2000, pp. 392–394.

(List continued on next page.)

*Primary Examiner*—C. Melissa Koslow
(74) *Attorney, Agent, or Firm*—Charles W. Calkins; Kilpatrick Stockton LLP

(57) ABSTRACT

The present invention provides new compositions containing colloidal nanocrystals with high photoluminescence quantum yields, new synthetic methods for the preparation of highly luminescent colloidal nanocrystals, as well as methods to control the photoluminescent properties of colloidal nanocrystals. The new synthetic methods disclosed herein allow photoemission brightness (quantum yield) to be correlated with certain adjustable nanocrystal growth parameters associated with a given synthetic scheme.

24 Claims, 6 Drawing Sheets

OTHER PUBLICATIONS

Shi, Jing, et al., [Abstract] "Magnetic Clusters in Molecular Beams, Metals, and Semiconductors," Science, vol. 271, Feb. 16, 1996, pp. 937–938.

Research Summary, http://web.mit.edu/chemistry/nanoclusters/research.html, Jul. 31, 2000.

Artemyev, Mikhail V., et al., "Light Trapped in a Photonic Dot: Microspheres Act as a Cavity for Quantum Dot Emission," Nano Letters, vol. 1, No. 6, 2001, pp. 309–314.

Brennan, J.G., et al., "Bulk and Nanostructure Group II–VI Compounds from Molecular Organometallic Precursors," Chem. Mater., vol. 2, No. 4, 1990, pp. 403–409.

Bruchez Jr., Marcel, et al., "Semiconductor Nanocrystals as Fluorescent Biological Labels," Science, vol. 281, Sep. 25, 1998, pp. 2013–2016.

Chan, Warren C. W., et al., "Quantum Dot Bioconjugates for Ultrasensitive Nonisotopic Detection," Science, vol. 281, Sep. 25, 1998, pp. 2016–2018.

Cumberland, Scott L., et al., "Inorganic Clusters as Single–Source Precursors for Preparation of CdSe, ZnSe, and CdSe/ZnS Nanomaterials," Chem. Mater., vol. 14, No. 4, 2002, pp. 1576–1584.

Dabbousi, B.O., et al., "(CdSe)ZnS Core–Shell Quantum Dots: Synthesis and Characterization of a Size Series of Highly Luminescent Nanocrystallites," J. Phys. Chem. B, vol. 101, No. 46, 1997, pp. 9463–9475.

Hines, Margaret A., et al., "Bright UV–Blue Luminescent Colloidal ZnSe Nanocrystals," J. Phys. Chem. B, vol. 102, No. 19, 1998, pp. 3655–3657.

Hines, Margaret A., et al., "Synthesis and Characterization of Strongly Luminescing ZnS–Capped CdSe Nanocrystals," J. Phys. Chem., vol. 100, No. 2, 1996, pp. 468–471.

Hoheisel, W., et al., "Threshold for quasicontinuum absorption and reduced luminescence efficiency in CdSe nanocrystals," J. Chem. Phys., vol. 101, No. 10, 1994, pp. 8455–8460.

Jun, Young–wook, et al., "Controlled Synthesis of Multi–armed CdS Nanorod Architectures Using Monosurfactant System," J. Am. Chem. Soc., vol. 123, No. 21, 2001, pp. 5150–5151.

Klimov, V. I., "Optical Gain and Stimulated Emission in Nanocrystal Quantum Dots," Science, vol. 290, Oct. 13, 2000, pp. 314–317.

Labella, V. P., et al., "Atomic Structure of the GaAs(001)–(2x4) Surface Resolved Using Scanning Tunneling Microscopy and First–Principles Theory," Physical Review Letters, vol. 83, No. 15, Oct. 11, 1999, pp. 2989–2992.

Lee, Jinwook, et al., "Full Color Emission from II–VI Semiconductor Quantum Dot–Polymer Composites" Adv. Mater., vol. 12, No. 15, Aug. 2, 2000, pp. 1102–1105.

Lemon, Buford I., et al., "Preparation and Characterization of Dendrimer–Encapsulated CdS Semiconductor Quantum Dots," J. Am. Chem. Soc., vol. 122, No. 51, 2000, pp. 12886–12887.

Murray, C.B., et al., "Synthesis and Characterization of Nearly Monodispensers CdE (E=S, Se, Te) Semiconductor Nanocrystallites," J. Am. Chem. Soc., vol. 115, 1993, pp. 8706–8715.

Norris, D.J., et al., "High–Quality Manganese–Doped ZnSe Nanocrystals," Nano Letters, vol. 1, No. 1, 2001, pp. 3–7.

Peng, Xiaogang, et al., "Epitaxial Growth of Highly Luminescent CdSe/CdS Core/Shell Nanocrystals with Photstabiliy and Electronic Accessibility," J. Am. Chem. Soc., vol. 119, No. 30, 1997, pp. 7019–7029.

Peng, Xiaogang, et al.; "Kinetics of II–VI and III–V Colloidal Semiconductor Nanocrystal Growth: 'Focusing ' of Size Distributions," J. Am. Chem. Soc., vol. 120, No. 21, 1998, pp. 5343–5344.

Peng, Xiaogang, et al., "Shape control of CdSe nanocrystals," Nature, vol. 404, Mar. 2, 2000, pp. 59–61.

Peng, Z. Adam, et al., "Formation of High–Quality CdTe, CdSe, and CdS Nanocrystals Using CdO as Precursor," J. Am. Chem. Soc., vol. 123, No. 1, 2001, pp. 183–184.

Peng, Z. Adam, et al., "Mechanisms of the Shape Evolution of CdSe Nanocrystals," J. Am. Chem. Soc., vol. 123, No. 7, 2001, pp. 1389–1395.

Pickett, Nigel L., et al., "Syntheses of Semiconductor Nanoparticles Using Single–Molecular Precursors," The Chemical Record, vol. 1, 2001, pp. 467–479.

Talapin, Dmitri V., et al., "Highly Luminescent Monodisperse CdSe and CdSe/ZnS Nanocrystals Synthesized in a Hexadecylamine–Trioctylphosphine Mixture," Nano Letters, vol. 1, No. 4, 2001, pp. 207–211.

Qu, Lianhua, et al., "Alternative Routes toward High Quality CdSe Nanocrystals," Nano Letters, vol. 1, No. 6, 2001, pp. 333–337.

Vossmeyer, T., et al., "CdS Nanoclusters: Synthesis, Characterization, Size Dependent Oscillator Strength, Temperature Shift of the Excitonic Transition Energy, and Reversible Absorbance Shift," J. Phys. Chem, vol. 98, No. 13, 1994, pp. 7665–7673.

* cited by examiner

COLLOIDAL NANOCRYSTALS WITH HIGH PHOTOLUMINESCENCE QUANTUM YIELDS AND METHODS OF PREPARING THE SAME

PRIOR RELATED U.S. APPLICATION DATA

This application claims priority to U.S. provisional application Ser. No. 60/308,727, filed Jul. 30, 2001.

STATEMENT OF GOVERNMENT LICENSE RIGHTS

This invention was made through the support of the National Science Foundation (Grant Nos. CHE0101178 and DMR0094248). The Federal Government may retain certain license rights in this invention.

TECHNICAL FIELD OF THE INVENTION

The present invention provides new compositions containing colloidal nanocrystals with high photoluminescence quantum yields, new synthetic methods for the preparation of highly luminescent colloidal nanocrystals, and new methods to impart control over the photoluminescent properties of as-prepared colloidal nanocrystals. Specifically, photoemission brightness (quantum yield), and various other nanocrystal properties such as monodispersity, can be correlated with certain adjustable nanocrystal growth parameters associated with a given synthetic scheme.

BACKGROUND OF THE INVENTION

Colloidal semiconductor nanocrystals have generated great fundamental interest in recent years and continue to exhibit tremendous promise for developing advanced materials. (Heath, J. R., Ed. *Acc. Chem. Res.* 1999; Alivisatos, A. P. *Science* 1996, 271, 933–937; Brus, L. E. *J. Chem. Phys.* 1986, 90, 2555) The size-dependent emission is probably the most attractive property of semiconductor nanocrystals. For example, differently sized CdSe nanocrystals can be prepared that emit from blue to red with very pure color. These nanocrystal-based emitters can be used for many purposes, such as light-emitting diodes, (Sundar, V. C.; Lee, J.; Heine, J. R.; Bawendi, M. G.; Jensen, K. F. *Adv. Mater.* 2000, 12, 1102; Schlamp, M. C.; Peng, X. G.; Alivisatos, A. P. *J. Appl. Phys.* 1997, 82, 5837–5842) lasers, (Artemyev, M.; Woggon, U.; R., W.; Jaschinski, H.; W., L. *Nano Lett.* 2001, 1, 309; Klimov, V. I.; Mikhailovsky, A. A.; Xu, S.; Malko, A.; Hollingsworth, J. A.; Leatherdale, C. A.; Eisler, H. J.; Bawendi, M. G. *Science* 2000, 290, 314–317) biomedical tags, (Han, M.; Gao, X.; Su, J. Z.; Nie, S. *Nat. Biotechnol.* 2001, 19, 631–635; Bruchez, M.; Moronne, M.; Gin, P.; Weiss, S.; Alivisatos, A. P. *Science* 1998, 281, 2013–2016; Chan, W. C. W.; Nie, S. M. *Science* 1998, 281, 2016–2018) and the like. For this reason, the control of the photoluminescence (PL) properties of semiconductor nanocrystals has been a major goal for developing the synthetic chemistry for colloidal semiconductor nanocrystals. In turn, the lack of viable synthetic methods that permit the desired level of control over the PL properties of semiconductor nanocrystals appears to have hampered progress in this area, and delayed the timely development of advanced applications for these unique materials.

The emission properties of semiconductor nanocrystals can be characterized by four fundamental parameters, namely the brightness, the emission color, the color purity, and the stability of the emission. Due to quantum size effects, (Brus, L. E. *J. Chem. Phys.* 1986, 90, 2555) the band gap of CdSe nanocrystals increases as their size decreases, and thus the emission color of the band-edge PL of the nanocrystals shifts continuously from red (centered around 650 nm) to blue (centered around 450 nm) as the size of the nanocrystals decreases. Because the emission color of a semiconductor nanocrystal is strongly dependent on its size (Brus, L. E. *J. Chem. Phys.* 1986, 90, 2555) and shape, (Peng, X. G.; Manna, L.; Yang, W. D.; Wickham, J.; Scher, E.; Kadavanich, A.; Alivisatos, A. P. *Nature* 2000, 404, 59–61) the color purity of the emission becomes dependent on the size and shape distribution of a nanocrystal sample. Therefore, the control of the emission color and color purity is likely a matter of the control of the size and shape, as well as size and shape distribution of the semiconductor nanocrystals, regarding which recent studies have provided a reasonable knowledge basis. (Peng, X. G.; Manna, L.; Yang, W. D.; Wickham, J.; Scher, E.; Kadavanich, A.; Alivisatos, A. P. *Nature* 2000, 404, 59–61; Peng, Z. A.; Peng, X. G. *J. Am. Chem. Soc.* 2001, 123, 1389–1395; Manna, L.; Scher, E. C.; Alivisatos, A. P. *J. Am. Chem. Soc.* 2000, 122, 12700–12706; Peng, X. G.; Wickham, J.; Alivisatos, A. P. *J. Am. Chem. Soc.* 1998, 120, 5343–5344; Murray, C. B.; Norris, D. J.; Bawendi, M. G. *J. Am. Chem. Soc.* 1993, 115, 8706–8715) The other two emission properties of brightness and emission stability, however, cannot yet be correlated with specific structural parameters or some adjustable nanocrystal growth condition associated with a given synthetic scheme. As a result, the PL brightness, measured by PL quantum yield (QY) or efficiency, and the stability of the emission of the "as-prepared" semiconductor nanocrystals are not easy to predict and generally vary from synthesis to synthesis. The ability to control a synthetic parameter such that PL efficiency (PL QY) of semiconductor nanocrystals could be boosted would be extremely valuable.

CdSe nanocrystals with relatively narrow size distributions (low polydispersity) and relatively high crystallinity became available in the early 1990s by use of dimethylcadmium as the cadmium precursor. (Murray, C. B.; Norris, D. J.; Bawendi, M. G. *J. Am. Chem. Soc.* 1993, 115, 8706–8715; Brennan, J. G.; Siegrist, T.; Carroll, P. J.; Stuczynski, S. M.; Reynders, P.; Brus, L. E.; Steigerwald, M. L. *Chem. Mater.* 1990, 2, 403) This organometallic approach has been further developed in terms of the control over the size, (Peng, X. G.; Wickham, J.; Alivisatos, A. P. *J. Am. Chem. Soc.* 1998, 120, 5343–5344) shape, (Peng, X. G.; Manna, L.; Yang, W. D.; Wickham, J.; Scher, E.; Kadavanich, A.; Alivisatos, A. P. *Nature* 2000, 404, 59–61; Peng, Z. A.; Peng, X. G. *J. Am. Chem. Soc.* 2001, 123, 1389–1395; Manna, L.; Scher, E. C.; Alivisatos, A. P. *J. Am. Chem. Soc.* 2000, 122, 12700–12706) and size/shape distribution of the resulting CdSe nanocrystals. More recently, alternative routes to CdSe have been developed using safe, inexpensive, and environmentally sound cadmium precursors and ligands, (Peng, X. *Chem. Eur. J.* 2002, 8, 334; Peng, Z. A.; Peng, X. *J. Am. Chem. Soc.* 2001, 123, 183–184; Qu, L.; Peng, Z. A.; Peng, X. *Nano Lett.* 2001, 1, 333) thereby providing a readily available synthetic method for CdSe nanocrystals. In principle, with knowledge regarding the control over the size/shape and size/shape distribution of CdSe nanocrystals, the emission color and the purity of the color can be controlled to a certain extent. However at present, the purity of the emission color of a CdSe nanocrystal sample is still significantly worse than that of the single particle emission. For example, the typical full width at half maximum (FWHM) of the PL peak of a CdSe nanocrystal ensemble at room temperature, is around 27–40 nm, (Sundar, V. C.; Lee, J.; Heine, J. R.; Bawendi, M. G.;

Jensen, K. F. *Adv. Mater.* 2000, 12, 1102; Talapin, D.; Rogach, A. L.; Kornowski, A.; Haase, M.; Weller, H. *Nano Lett.* 2001, 1, 207) noticeably broader than that observed by single dot spectroscopy (typically <20 nm). (Heath, J. R., Ed. *Acc. Chem. Res.* 1999) These data indicate the relatively nonhomogeneous emission properties of the nanocrystals within the sample.

The control over the PL QY and emission stability of the CdSe nanocrystals synthesized through either the traditional organometallic approach or the alternative routes also remains rather poor. For example, the best PL QY reported for the as-prepared nanocrystals at room temperature is around 20% in the wavelength range between 520 and 600 nm, and only a few percent or lower in the wavelength regions above 600 nm and below 520 nm. (Sundar, V. C.; Lee, J.; Heine, J. R.; Bawendi, M. G.; Jensen, K. F. *Adv. Mater.* 2000, 12, 1102; Qu, L.; Peng, Z. A.; Peng, X. *Nano Lett.* 2001, 1, 333; Talapin, D.; Rogach, A. L.; Kornowski, A.; Haase, M.; Weller, H. *Nano Lett.* 2001, 1, 207) Neither the stability nor the reproducibility of the PL QY are predictable using current synthetic methods. (Qu, L.; Peng, Z. A.; Peng, X. *Nano Lett.* 2001, 1, 333) With some inorganic and organic surface passivation following synthesis, the PL QY of CdSe nanocrystals can be boosted to as high as over 50% in the 520–600 nm window, (Talapin, D.; Rogach, A. L.; Komowski, A.; Haase, M.; Weller, H. *Nano Lett.* 2001, 1, 207; Peng, X. G.; Schlamp, M. C.; Kadavanich, A. V.; Alivisatos, A. P. *J. Am. Chem. Soc.* 1997, 119, 7019–7029; Dabbousi, B. O.; Rodriguez-Viejo, J.; Mikulec, F. V.; Heine, J. R.; Mattoussi, H.; Ober, R.; Jensen, K. F.; Bawendi, M. G. *J. Phys. Chem. B* 1997, 101, 9463–9475; Hines, M. A.; Guyot-Sionnest, P. *J. Phys. Chem.* 1996, 100, 468) but the efficiency for the orange-red color window is still quite low. This problem is especially severe for red emissions (around 650 nm), where the PL QY of nanocrystals in solution is nearly zero, like the present, as-prepared CdSe nanocrystals. (Sundar, V. C.; Lee, J.; Heine, J. R.; Bawendi, M. G.; Jensen, K. F. *Adv. Mater.* 2000, 12, 1102; Talapin, D.; Rogach, A. L.; Komowski, A.; Haase, M.; Weller, H. *Nano Lett.* 2001, 1, 207)

Therefore, what is needed are new methods to prepare semiconductor nanocrystals that afford the ability to boost and control the photoluminescence quantum yield (PL QY) of as-prepared samples, especially for CdSe nanocrystals. If possible, these methods would allow manipulation of the purity of the emission color, by controlling the full width at half maximum (FWHM) of the nanocrystal PL peak. It is also desirable to develop methods that could provide emission peaks sufficiently sharp so as to approach those observed by single dot spectroscopy (in the 20 nm range). Due to the failure of orange-red emitting materials in general, efforts are especially needed for materials that emit in the wavelength region from about 600 nm (orange) to about 650 nm (red). To accomplish these difficult goals of controlling and tuning the photoluminescence (PL) properties of CdSe, as well as other semiconductor nanocrystals, it would also be desirable to obtain detailed information that correlated nanocrystal growth parameters with emission properties. The present invention demonstrates that, despite previous failures to control PL properties, especially the PL QY, of semiconductor nanocrystals, such control is possible, and can be readily correlated with synthesis and crystallization parameters.

SUMMARY OF THE INVENTION

The present invention addresses the current limitations in nanocrystal photoluminescence quantum yield (PL QY) by providing colloidal nanocrystals that, in their as-prepared state, luminesce between about 550–675 nm (inclusive) with a photoluminescence quantum yield (PL QY) greater than or equal to about 40%. In some embodiments, the colloidal nanocrystals of this invention luminesce between about 600–650 nm (inclusive) with a PL QY from about 50% to about 80%. As-prepared nanocrystals ranging in size from about 1–6 nm (inclusive) in average diameter are typical, with the size range of these nanocrystals being very monodisperse. The high monodispersity that can be achieved in this invention is seen in the photoluminescence emission line of the nanocrystals, which can have a full width at half maximum (FWHM) as narrow as 23–24 nm. The as-prepared nanocrystals described herein are further characterized by the wavelength difference ($\Delta\lambda$) between the photoluminescence emission line of the nanocrystals at the "bright point" of highest PL QY ($\lambda_b$), and the photoluminescence emission line of the nanocrystals at the minimum full width at half maximum ($\lambda_m$). This wavelength difference, $\Delta\lambda = \lambda_b - \lambda_m$, for those nanocrystals with the highest PL QY is found to be greater than or equal to about 0. Further, this invention encompasses new products and devices incorporating these nanocrystals, such as light-emitting diodes, biological labeling agent such as biomedical tags, photoelectric devices including solar cells, catalysts, lasers, and the like. As understood by one of ordinary skill in the art, prior nanocrystal syntheses typically require additional processing or size sorting steps after crystallization to achieve the desired size, size distribution, and other properties of the sample. The present invention affords improved sizes, size distributions, photoluminescence quantum yields, and related physical and chemical properties of the colloidal nanocrystals in their "as-prepared" state, without the need for size sorting or further processing steps.

The present invention further addresses the existing limitations in PL quantum yield (PL QY) of colloidal nanocrystals by providing a synthetic system that generates CdSe nanocrystals with improved emission properties. These new preparative methods correlate reaction conditions with PL QY, thereby imparting the ability to control and tune quantum yield, as well as other nanocrystal properties. This capability affords the production of extremely "bright" CdSe nanocrystals, and further allows the selection of desired brightness (or quantum yield) within certain ranges, by adjusting particular reaction parameters. This invention also allows control of the emission color purity (as evidenced by the width of the nanocrystal PL peak), and to provide nanocrystal samples with extremely sharp emission peaks due to sample homogeneity. These methods are demonstrated in the orange-to-red wavelength region (about 600 nm to about 650 nm), but are applicable to other regimes as well. Importantly, nanocrystal growth parameters can be correlated with these emission properties for designing and tailoring nanocrystal properties. The methods described herein are applicable to a number of semiconductor materials, including many metal chalcogenides.

In one embodiment, this invention involves a method of synthesizing semiconductor nanocrystals with an improved photoluminescence quantum yield, by combining a cation precursor, a first ligand, and a first solvent to form a cation-ligand complex, and then this cation-ligand complex with an anion precursor. Typically the anion precursor is in solution in a second solvent through its reaction with a second ligand, forming an anion-ligand complex. The cation complex and the anion complex are then admixed at one temperature sufficient to induce reaction between them, followed by adjusting the temperature of the mixture to a second temperature sufficient to form nanocrystals of the reaction product. Importantly, synthesizing semiconductor nanocrystals with high photoluminescent quantum yields (PL QY) requires a significant excess of one of the precursors, either the anion or the cation. A large excess of the anion precursor is typical. For CdSe nanocrystal formation, the highest PL QY values are obtained at the lowest Cd:Se ratios. The present invention further encompasses a composition that includes colloidal nanocrystals prepared by the method described above.

The cation precursors used in the methods disclosed herein can be elements, covalent compounds, or ionic compounds, including coordination complexes or metal salts, that serve as a source for the electropositive element or elements in the resulting nanocrystal. When feasible, inexpensive and safe compounds such as metal oxides are preferred. Anion precursors can also be elements, covalent compounds, or ionic compounds that serve as a source for the electronegative element or elements in the resulting nanocrystal. Inexpensive and safe compounds, such as naturally occurring substances, also constitute the preferred anion precursors. These definitions anticipate that ternary compounds, quaternary compounds, and even more complex species may be prepared using the methods disclosed herein, in which case more than one cation precursor and/or more than one anion precursor are typically required.

Generally, the methods disclosed herein are applicable to nanocrystals prepared using a range of cation precursor compounds, for example, precursors of the group II metals (for example, Zn, Cd, or Hg), the group III metals (for example, Al, Ga, or In), the group IV metals (for example, Ge, Sn or Pb), or the transition metals (for example, Ti, Zr, Hf, V, Nb, Ta, Cr, Mo, W, Mn, Tc, Re, Fe, Co, Ni, Pd, Pt, Rh, and the like). (See, F. A. Cotton et al., Advanced Inorganic Chemistry, 6th Edition, (1999).) The cation precursor can constitute a wide range of substances, such as a metal oxide, a metal carbonate, a metal bicarbonate, a metal sulfate, a metal sulfite, a metal phosphate, metal phosphite, a metal halide, a metal carboxylate, a metal alkoxide, a metal thiolate, a metal amide, a metal imide, a metal alkyl, a metal aryl, a metal coordination complex, a metal solvate, a metal salt, and the like. In a typical preparation, the ligand is selected from fatty acids, amines, phosphines, phosphine oxides, phosphonic acids, or combinations of these compounds. Anion precursors are most often selected from the element itself (oxidation state 0), covalent compounds, or ionic compounds.

The nanocrystals of this invention typically constitute metal chalcogenides such as CdSe, CdTe, ZnSe, and the like. Thus, anion precursors used in this invention are most often precursors containing chalcogens. Many embodiments of this invention utilize the elemental chalcogens themselves (such as S, Se, or Te) as the anion precursor.

For example, a typical synthesis of CdSe nanocrystals with high photoluminescence (PL) efficiency used CdO as the cation precursor, which was dissolved in a fatty acid such as stearic acid, and diluted with a primary amine, such as hexadecylamine (HDA). A cosolvent such as trioctylphosphine oxide (TOPO) can be used in the cation precursor solution, but is not required. This mixture is heated to around 320° C. while a solution of elemental selenium dissolved in tributylphosphine ("Se-TBP"), optionally with a cosolvent such as dioctylamine, is injected. After injection, the solution temperature was maintained at about 290° C. for growth of the nanocrystals. At various time intervals during the reaction, aliquots of the reaction mixture were removed and diluted with chloroform and used to obtain the spectroscopic data provided herein.

Among the most important experimental parameters discovered that allowed tailoring of nanocrystal properties is the initial cation:anion, here Cd:Se, molar ratio of the precursors in the reaction solution. Importantly, a typical synthesis employed a large excess of either the anion precursor or the cation precursor. For the preparation of CdSe, the initial Cd:Se molar ratio of the precursors in the solution ranged from about 1:20 to about 2:1. Using an excess of selenium precursor provided greater processing advantages, and therefore excess anion precursor was more often used. Typically, the Cd:Se ratio used was from about 1:10 to about 1:5. This large excess of anion precursor (or anion-ligand complex) as compared to cation precursor provided a striking boost of the PL QY of the as-prepared CdSe nanocrystals, which reached up to around 80% and was independent of the excitation wavelength.

The use of variable cation:anion ratios presents significant design advantages in the preparation of nanocrystals, perhaps because selected ratios allow the reactivity of precursor monomers to be "tuned" in various ways. It may be possible that the boost of the PL QY values is a signature of an optimal surface structure/reconstruction of the semiconductor nanocrystals grown under certain conditions. While not intending to be bound by the following statement, it is thought that when a nanocrystal growth reaction occurs under conditions in which monomer reactivity is moderated, and exhibits only a limited tendency to add to the surface of small nanocrystals (early in the reaction) or to depart the surface of the larger nanocrystals (late in the reaction), surface structure/reconstruction is most favorable and high PL QY values result. This potential is explicitly demonstrated herein with successful synthetic schemes for producing high quality, monodisperse, and extremely bright nanocrystals of CdSe.

Accordingly, it is one aspect of the present invention to provide new synthetic methods for preparing semiconductor nanocrystals that are characterized by high photoluminescence quantum yields.

It is another aspect of this invention is discovery of a method to correlate reaction conditions with the resulting PL QY of a semiconductor nanocrystal, and to thereby impart control over nanocrystal quantum yield.

Still another aspect of the present invention is the development of new synthetic methods for preparing semiconductor nanocrystals that are highly monodisperse.

It is a further aspect of this invention to provide a method for control over the stability of the photoluminescence emission of as-prepared semiconductor nanocrystals.

Yet another aspect of the present invention is the development of a method of to control the purity of the emission color of as-prepared semiconductor nanocrystals.

Still another aspect of this invention is developing means to select the desired photoluminescent brightness (or quantum yield) of a semiconductor nanocrystal a within certain ranges, by adjusting reaction parameters.

A further aspect of this invention is the correlation of nanocrystal growth parameters with nanocrystal emission properties for designing and tailoring nanocrystal properties.

Yet another aspect of this invention is to prepare monodisperse CdSe nanocrystals that are highly luminescent in the orange-to-red wavelength region, with quantum yields of approximately 80%.

These and other features, aspects, objects and advantages of the present invention will become apparent after a review

DETAILED DESCRIPTION OF THE INVENTION

Figure 1:
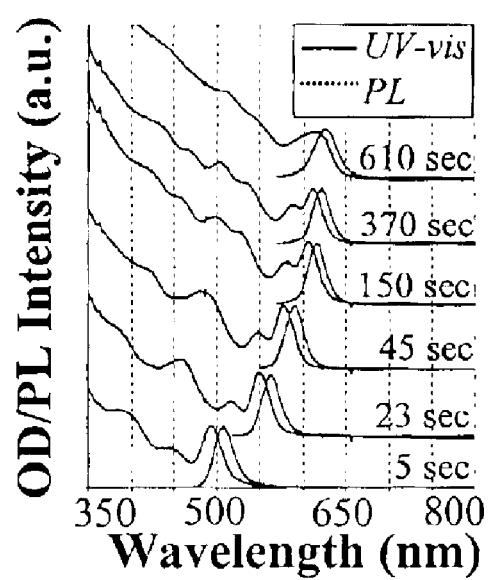
FIG. 1 illustrates the temporal evolution of the UV-vis absorption and PL spectra of CdSe nanocrystals under the reaction conditions provided in the detailed description section below, and in the typical synthesis disclosed in Example 2. The reaction time after the injection for each sample is also given in the plot.

The present invention provides semiconductor nanocrystals with tailored and enhanced photoluminescence quantum yields (PL QY). In particular, this invention addresses the current limitations in PL QY of semiconductor nanocrystals by providing a synthetic strategy that generates as-prepared CdSe nanocrystals with greatly improved emission properties. These new preparative methods correlate reaction conditions with PL QY thereby imparting the ability to control and tune PL QY or other nanocrystal properties.

Improved Synthetic Procedures

The synthetic procedure of this invention is generally described as follows. In one embodiment, a cation-ligand solution is provided by combining a cation precursor, a first ligand, and a first solvent to form a cation-ligand complex. Typically, an anion-ligand solution is similarly formed by combining an anion precursor with a second ligand and a second solvent. In another aspect of this invention, the anion precursor is combined with a second ligand, a second solvent, or a combination thereof, prior to admixing with the cation-ligand complex. The cation-ligand complex and the anion-ligand complex are than admixed at a first temperature sufficient for reaction to occur. In order to boost the PL quantum yield to the desired level, the concentration of one precursor, either the anion-ligand complex (anion precursor) or the cation-ligand complex (cation precursor) in the initial reaction mixture, is typically present in about a 2-fold to 20-fold concentration excess of the other precursor. In another aspect, the initial concentration of either the anion or the cation precursor is at least about 2 times the initial concentration of the other precursor in the mixture. Usually, the anion precursor is present in excess of the cation precursor. The temperature of the reaction mixture is then adjusted to a second temperature sufficient to form nanocrystals of the reaction product. Optionally, a cosolvent may be used to depress the solidification rate during sampling and further increase the reaction temperature.

Cation precursors can be elements, covalent compounds, or ionic compounds, including coordination complexes or a metal salt, that serve as a source for the electropositive element or elements in the resulting nanocrystal. When feasible, inexpensive and safe compounds such as metal oxides are preferred. Anion precursors can also be elements, covalent compounds, or ionic compounds that serve as a source for the electronegative element or elements in the resulting nanocrystal. Inexpensive and safe compounds, such as naturally occurring substances, also constitute the preferred anion precursors. These definitions anticipate that ternary compounds, quaternary compounds, and even more complex species may be prepared using the methods disclosed herein, in which case more than one cation precursor and/or more than one anion precursor are typically required.

In a typical reaction, large monodisperse CdSe nanocrystals were sought, because they emit in the orange-to-red window. (Qu, L.; Peng, Z. A.; Peng, X. *Nano Lett.* 2001, 1, 333) The use of stearic acid as a ligand was proven to be helpful for the formation of large-sized CdSe nanocrystals. Thus, CdO was employed as the cation precursor, which was dissolved in a fatty acid such as stearic acid to form calcium stearate. Primary amines provided the best results and were typically used as a solvent for the cation-ligand complex. Cadmium stearate in amines was found to be sufficiently robust at the high temperatures required for the formation of semiconductor nanocrystals with high structural quality. Trioctylphosphine oxide (TOPO) was found to be a good cosolvent to depress the solidification rate of the reaction mixture during sampling and to further increase the reaction temperature, although it was not a requirement of this reaction. (Qu, L.; Peng, Z. A.; Peng, X. *Nano Lett.* 2001, 1, 333) The experimental results revealed that this chosen system indeed generated large CdSe nanocrystals emitting well in red.

While stearic acid (SA; $C_{18}H_{36}O_2$) constituted an excellent ligand when CdO was used as the cation precursor, other fatty acids with different chain lengths (and consequently, different boiling points) could be used in this invention. For example, decanoic acid (DA; $C_{10}H_{20}O_2$), lauric acid (LA; $C_{12}H_{24}O_2$), myristic acid (MA; $C_{14}H_{28}O_2$), palmitic acid (PA; $G_{16}H_{32}O_2$), oleic acid (OA; $C_{18}H_{34}O_2$), or a combination thereof could also be used. However, for the preparation of high PL QY CdSe nanocrystals, SA was typically employed.

Importantly, a typical synthesis employed a large excess of one precursor over the other, usually an excess of the selenium precursor. For example, the initial Cd:Se molar ratio of the precursors in the solution was usually equal to about 1:10. This large excess of anion precursor (or anion-ligand complex) as compared to cation precursor provided a striking boost of the PL QY of the as-prepared CdSe nanocrystals, which reached up to about 80% (FIGS. 1 and 2) and was independent of the excitation wavelength. Initial Cd:Se molar ratio of the precursors could range from about 1:20 to about 2:1 to afford substantial improvements to the PL QY. Typically, superior boosts to the PL QY of as-prepared CdSe nanocrystals were obtained with initial Cd:Se ratios ranging from about 1:5 to about 1:10.

Figure 2:
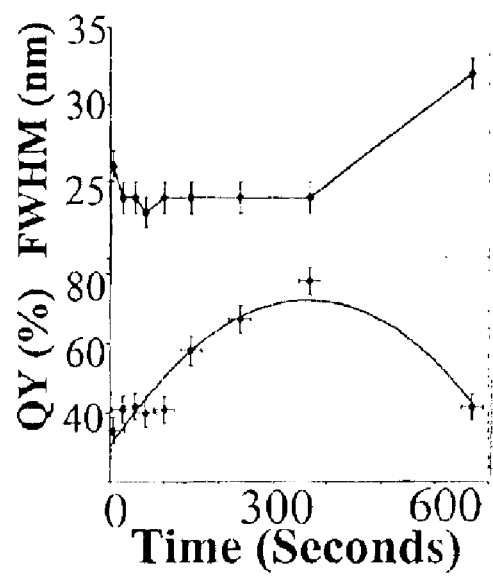
FIG. 2 demonstrates the temporal evolution of the PL QY values (bottom panel) at different reaction times for the same reaction shown in FIG. 1. The FWHM values of the PL spectra (top panel) at different reaction times for the same reaction are also provided. Trend lines (solid lines) are added for each plot to guide the eyes.

FIG. 1 demonstrates the temporal evolution of the UV-vis absorption and PL spectra of CdSe nanocrystals under the reaction conditions provided in Example 2, with a Cd:Se molar ratio of 1:10. The time of reaction after injection of the anion solution for each sample is also given in the plot. These UV-vis absorption and PL spectra of the several samples shown in FIG. 1 are extremely sharp, with about 23–24 nm of their FWHM of the PL spectra and up to 6–7 features of the absorption spectra, further indicating sample homogeneity. FIG. 2 (bottom panel) presents the temporal evolution of the PL QY values as the reaction proceeds, for the same reaction shown in FIG. 1, while FIG. 2 (top panel) illustrates the FWHM values of the PL spectra at the different reaction times for the same reaction shown in FIG. 1, which are discussed below. Thus, in one aspect, the present invention provides a composition comprising colloidal nanocrystals, wherein the full width at half maximum of the photoluminescence emission line of the as prepared nanocrystals is from about 20 nm to about 30 nm. In another aspect, the as-prepared nanocrystals are characterized by a full width at half maximum of the photoluminescence emission line from about 20 nm to about 25 nm. In yet another aspect, the as-prepared nanocrystals are characterized by a full width at half maximum of the photoluminescence emission line from about 23 to about 25 nm, or from about 23 nm to about 24 nm, as indicated in FIGS. 1 and 2.

Photoluminescence (PL) Bright Point and "Focusing" the Nanocrystal Size Distribution The temporal evolution of the PL QY and the full width at half maximum (FWHM) of the PL peak of the as-synthesized CdSe nanocrystals of the reaction shown in FIG. 1 is plotted in FIG. 2. Thus, FIG. 2 (bottom) presents PL QY values at the different reaction times while FIG. 2 (top) illustrates the FWHM values of the PL spectra at the different reaction times, both for the same reaction shown in FIG. 1. The PL QY plot of the as-prepared nanocrystals increased monotonically to a maximum and then gradually decreased (FIG. 2, bottom). For convenience, the position with the maximum PL QY will be termed the "PL bright point" or simply, the "bright point".

The FWHM plot of the PL spectrum (in wavelength) possessed a minimum (FIG. 2, bottom). This temporal window is referred to as a "focusing" of nanocrystal size distribution. Peng, X. G.; Wickham, J.; Alivisatos, A. P. J. Am. Chem. Soc. 1998, 120, 5343–5344) Focusing the size distribution, as indicated by the sharpening of the absorption features and narrowing of the photoluminescence (PL) peak over time, was observed shortly after injection of the anion solution. Thus, the nanocrystal sample became more monodisperse as the reaction initiated, followed by a gradual "defocusing" of the nanocrystal size distribution. The instantaneous appearance of a focusing window after the initiation of the reaction indicates that the nucleation occurred in a very short period of time, after which substantially all of the nuclei formed grew at substantially the same time due to the relatively high concentrations of the remaining monomers after the nucleation process. Thus, focusing arises from smaller nanocrystals growing at a faster rate than larger nanocrystals, such that size distribution narrows.

As seen by comparing the evolution of PL QY values and FWHM values, the bright point and the minimum point of the PL FWHM (focusing point) did not overlap for this reaction. Thus, the brightest sample exhibiting the maximum PL QY does not correspond to the most monodisperse sample with the minimum FWHM.

Figure 3:
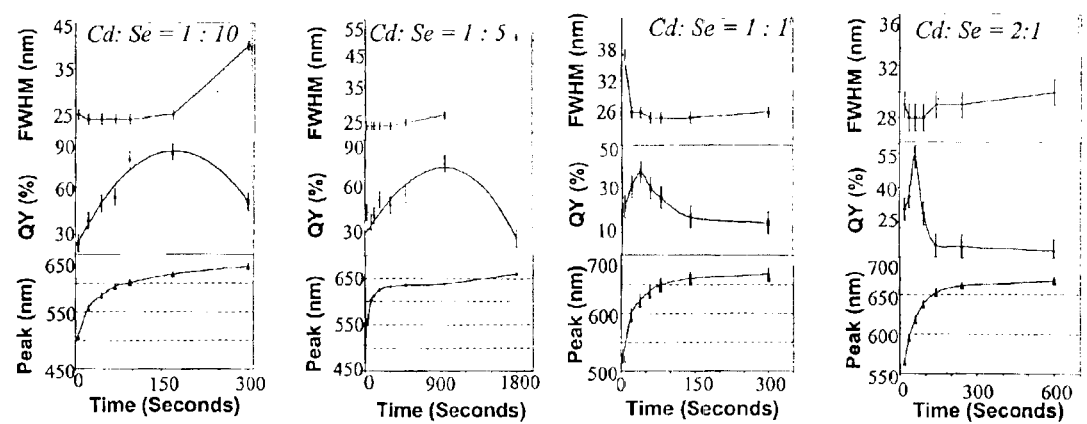
FIG. 3 displays the temporal evolution of the FWHM, the PL QY and the PL peak position for four different reactions, each of which was carried out with different initial Cd:Se ratios of the precursors as shown in the plot. For all four reactions, the initial concentration product of the two precursors was fixed as 1411 (mmol/kg)$^2$. The other conditions were the same as those of the typical synthesis disclosed in Example 2. Trend lines (solid lines) are added for each plot to guide the eyes.
Figure 4:
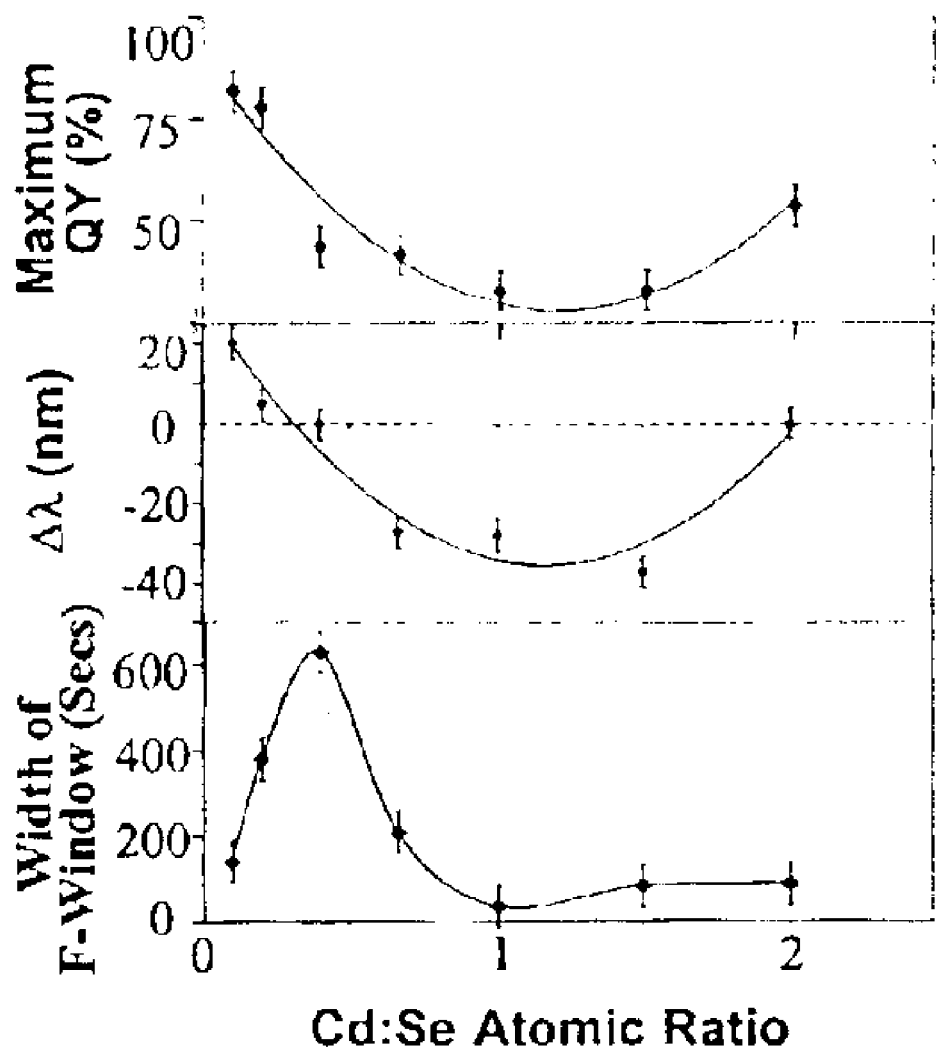
FIG. 4. Maximum PL QY (top panel), $\Delta\lambda$ (middle panel), and reaction time needed to reach the PL bright point (bottom panel) versus the initial Cd:Se ratio of the precursors. $\Delta\lambda(nm)=\lambda_b-\lambda_m$ where $\lambda_b$ and $\lambda_m$ are the wavelengths at the bright point and the minimum point of the PL FWHM, respectively. For all reactions, the initial concentration product of the two precursors was fixed as 1411 (mmol/kg)$^2$.

As described below, the relative position of the bright point and the minimum point of the PL FWHM varied significantly when the initial Cd:Se ratio of the precursors in a reaction was changed (FIGS. 3 and 4). The existence of a PL bright point was observed to be a general phenomenon for different types of semiconductor nanocrystals with different shapes or grown in different solvent systems. The current system is the best one for studying this phenomenon because of the high PL QY and the small FWHM of the PL spectra of the resulting nanocrystals, and clearly demonstrates how to control the PL QY of the as-prepared semiconductor nanocrystals.

Photoluminescence Quantum Yield (PL QY) and Full-Width at Half Maximum (FWHM) of the Photoluminescence Peak Versus Initial Cd:Se Precursor Ratio The PL QY of CdSe nanocrystals does not appear to be very sensitive to the imperfections of the crystallinity of the nanocrystals caused by stacking faults. For example, the PL QY of wurtzite CdSe nanocrystals with almost no stacking faults, showed little difference with the PL QY of those with some zinc blende stacking faults in each nanocrystal. Murray, C. B.; Norris, D. J.; Bawendi, M. G. J. Am. Chem. Soc. 1993, 115, 8706–8715; Qu, L.; Peng, Z. A.; Peng, X. Nano Lett. 2001, 1, 333; Qu, L.; Peng, Z. A.; Peng, X. Nano Lett. 2001, 1, 333) In contrast, the PL QY does appear to be sensitive to the surface environment of the nanocrystals. For instance, certain types of organic ligands or inorganic passivation (Qu, L.; Peng, Z. A.; Peng, X. Nano Lett. 2001, 1, 333; Qu, L.; Peng, Z. A.; Peng, X. Nano Lett. 2001, 1, 333; Peng, X. G.; Schlamp, M. C.; Kadavanich, A. V.; Alivisatos, A. P. J. Am. Chem. Soc. 1997, 119, 7019–7029; Dabbousi, B. O.; Rodriguez-Viejo, J.; Mikulec, F. V.; Heine, J. R.; Mattoussi, H.; Ober, R.; Jensen, K. F.; Bawendi, M. G. J. Phys. Chem. B 1997, 101, 9463–9475; Hines, M. A.; Guyot-Sionnest, P. J. Phys. Chem. 1996, 100, 468) on the surface of nanocrystals have improved the PL QY of semiconductor nanocrystals dramatically. While not intending to be bound by the following statement, we believe that control of the nanocrystal surface structure, probably a reconstructed surface, of semiconductor nanocrystals themselves may be very important for controlling and improving their PL properties.

Traditional preparative methods for colloidal CdSe nanocrystals usually employ cadmium and selenium precursors in an atomic ratio of close to 1:1, although the chemical reactivities of the two precursors can be significantly different. Disclosed herein are experimental results that unambiguously reveal that the initial Cd:Se ratio of the precursors is a determining factor for the emission properties of the as-synthesized nanocrystals, possibly through control of the nanocrystal surface structure itself.

The results illustrated in FIG. 3 are from four representative reactions among one series of experiments, in which the initial Cd:Se ratio was varied from between about 2:1 and about 1:10. In all reactions shown in FIG. 3, the concentration product of the initial cadmium and selenium precursors was maintained at a constant value of 1411 (mmol/kg)$^2$. In reactions employing a large excess of Cd (for example, greater than about 3:1), it was difficult to initiate and execute a growth reaction. In these reactions, only very small amounts of nuclei were formed over a relatively long period of time and these nuclei grew very fast to insoluble, large sizes.

FIG. 3 also demonstrates that each individual reaction possessed a minimum PL FWHM at some point during the progress of the reaction. The minimum value of the PL FWHM gradually increased as the initial Cd:Se ratio of the precursors increased from 1:10 to 2:1. The average nanocrystal size associated with that PL FWHM minimum point also increased as the initial Cd:Se precursor ratio increased, as indicated by the relative PL peak positions. The temporal evolution of the PL QY can be classified according one of two types. The reactions using an excess of the selenium precursor, where the initial Cd:Se molar ratios were 1:10 and 1:5, demonstrated a pattern similar to that of the reaction shown in FIG. 2, characterized by a relatively flat PL bright point, a positive wavelength difference between the bright point and the minimum point of the PL FWHM, that is, $\Delta\lambda(nm)=\lambda_b-\lambda_m>0$, and a relatively high PL QY at the bright point. The other two reactions, with the initial Cd:Se precursor molar ratios of 2:1 and 1:1, differed from the excess selenium reactions in several respects. First, the PL QY values at the bright point in these reactions were significantly lower than those reactions using excess selenium. Second, the bright points of these reactions exhibited sharp maxima instead of relatively flat ones. Third, the bright point overlapped with the minimum point of the PL FWHM for the reaction with 2:1 initial Cd:Se ratio, and it appeared at the short-wavelength side of the minimum point of the PL FWHM for the reaction started with a Cd:Se ratio of 1:1. Thus, for these two Cd:Se ratio reactions, the wavelength difference between the bright point and the minimum point of the PL FWHM, that is, $\Delta\lambda(nm)=\lambda_b-\lambda_m\leq 0$. Therefore, in order to boost the PL QY of as-prepared CdSe nanocrystals, an excess of either Cd or Se may be used; typically the Cd:Se ration is controlled to between about 1:20 to about 2:1. The atomic (or molar) ratio of Cd:Se is typically controlled to between about 1:10 and about 1:5.

The influence of the initial Cd:Se precursor ratio on the PL properties of the CdSe nanocrystals shown in FIG. 3 can be further understood by examining FIG. 4. The top panel in FIG. 4 summarizes the relationship between the PL QY at the bright point versus the initial Cd:Se ratio of the precursors in the solution. This plot demonstrates that a significant excess of one of the precursors promoted the formation of CdSe nanocrystals with a high PL QY. This plot further demonstrates that the highest PL QY values at the bright point were obtained at the lowest Cd:Se ratios.

The middle panel of FIG. 4 illustrates the trend of $\Delta\lambda(nm)$ versus the initial Cd:Se ratio of the precursors, where $\Delta\lambda=\lambda_b-\lambda_m$, and where $\lambda_b$ and $\lambda_m$ are the wavelength values at the bright point and the minimum point of the PL FWHM, respectively. This plot demonstrates that the highest PL QY values at the bright point were obtained at values of $\Delta\lambda$ that were the most positive.

The reaction time needed to reach the PL bright point for each reaction is plotted in the bottom panel of FIG. 4, which indicates that a high PL QY is not simply associated with the reaction time.

Within the reaction conditions tested, all of the trends shown in FIG. 4 were repeatedly observed. All experiments shown in FIGS. 3 and 4 were performed under the same conditions, with the initial concentration product of the two precursors maintained constant (at 1411 (mmol/kg)$^2$). Similar results were also obtained by fixing the concentration of either the cadmium or selenium precursor equal to 0.0167 mol/kg and varying the concentration of the other precursor, such that the initial concentration product of the two precursors was not constant.

Photoluminescence Quantum Yield (PL QY) Versus Photoluminescence (PL) Peak Position Although most of the synthetic efforts focused on the growth of CdSe nanocrystals emitting in the orange-to-red window, results indicate that the method and the concept of PL QY control can be extended to the synthesis of CdSe nanocrystals emitting other visible colors. As disclosed herein, this control may be attained by varying the total concentration of the initial precursors, the types of precursors, the solvent system, the reaction and crystallization temperatures, and the growth time.

Figure 5:
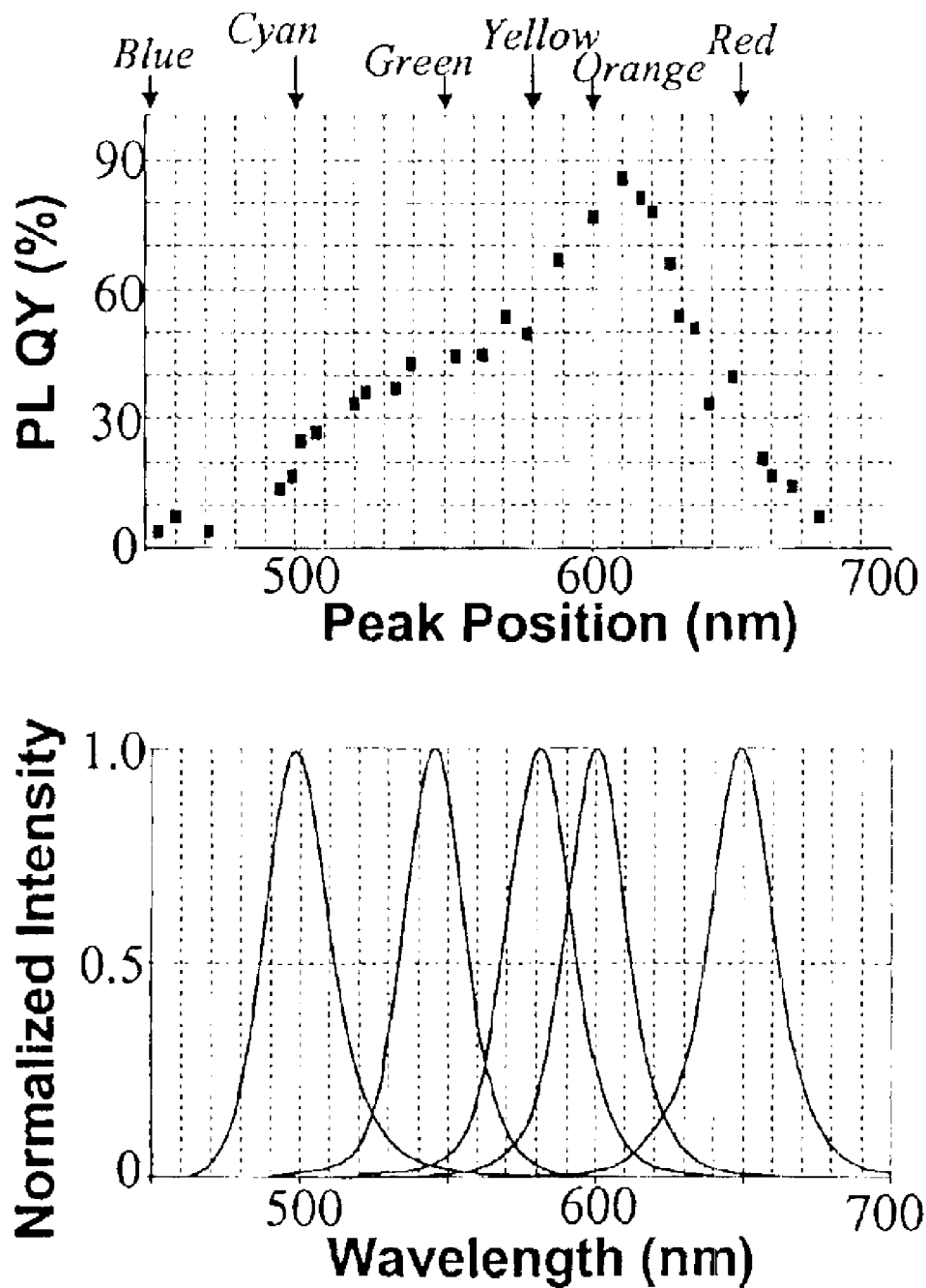
FIG. 5 illustrates the PL QY of different-sized CdSe nanocrystals plotted against their emission peak positions (top panel), and the PL spectra of several CdSe nanocrystal samples at different emission positions (bottom panel).

The achieved PL QY of the as-synthesized CdSe nanocrystals is plotted against their emission peak position in FIG. 5, top panel. For each data point, the corresponding y- and x-axis values respectively represent the PL QY and the emission peak position of that given sample. The PL spectra of representative CdSe nanocrystal samples with different emission colors are also demonstrated in FIG. 5, bottom panel. In comparison to the as-prepared CdSe nanocrystals reported previously, the CdSe nanocrystals shown in FIG. 5 possess significantly greater PL QY and narrower emission peak width. Thus, using the methods disclosed herein, CdSe nanocrystals displaying brighter PL spectra and greater monodispersity are obtained as compared to previously available samples. Even for those samples which emit around 500 nm (cyan) and those that emit around 680 nm (red-to-infrared), for which PL QY is about 30% and below, most of these samples exhibit greater PL QY and more narrow emission peaks than those exhibited in previously known, as-prepared samples.

Stability of Nanocrystal Optical Properties

The PL properties of the as-prepared CdSe nanocrystals, including the PL QY, the peak position, and the PL FWHM, did not show any detectable change upon aging in air for several months, if no precipitation occurred. Occasionally, the nanocrystals precipitated out of the solution, indicating the loss of surface ligands. If this occurred, the precipitated aggregates normally could not be redispersed in solution, even with the addition of primary amines. However as described in Example 2, by adding methanol or acetone into the chloroform solution of the as-prepared CdSe nanocrystals, the precipitation of the nanocrystals from their concentrated solutions could be performed without damaging the optical properties of the nanocrystals. Such a precipitation process, however, decreased the PL QY of the precipitated nanocrystals and the nanocrystals became gradually insoluble if precipitation and dissolution were repeated several times. This observation suggests that repeated precipitation and dissolution may removed some of the primary amine ligands from the nanocrystal surface.

Figure 7:
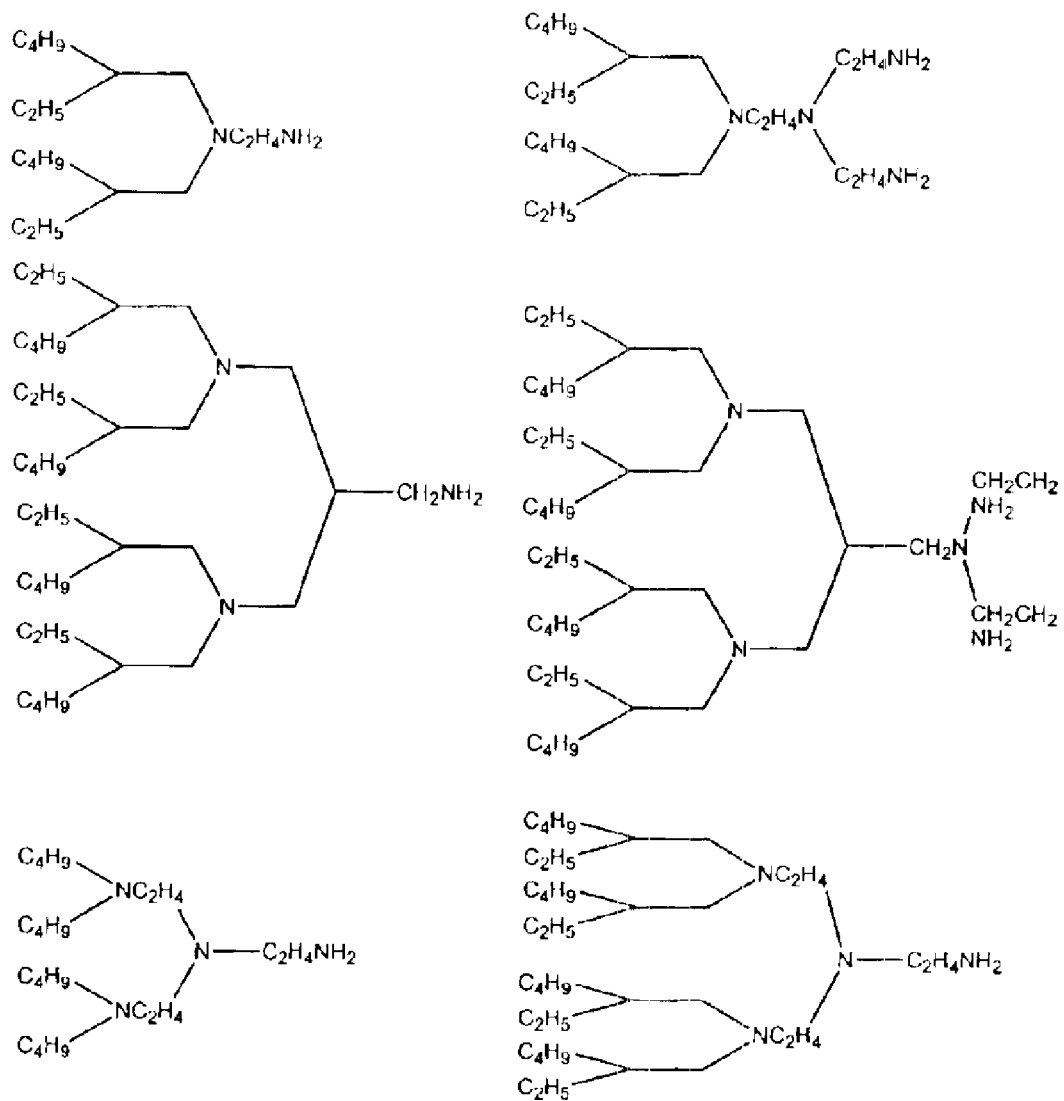
FIG. 7 illustrates some representative examples of dendron ligands containing coordinating amine nitrogen atoms which function as relatively non-labile, stabile ligands, and provide the required kinetic and thermodynamic stability for colloidal nanocrystals such as CdSe.

It has been reported that amines are not particularly strong ligands to CdSe nanocrystals and are quite labile on the surface of the nanocrystals. (Peng, X. G.; Schlamp, M. C.; Kadavanich, A. V.; Alivisatos, A. P. *J. Am. Chem. Soc.* 1997, 119, 7019–7029.) To solve this stability issue associated with ligand loss, flexible dendron ligands with an amine group at their focal point should provide the required kinetic and thermodynamic stability and function as relatively non-labile, stabile ligands for CdSe nanocrystals. Examples of these ligands are presented in FIG. 7.

Nanocrystal Shape, Crystal Structure, and Composition

Figure 6:
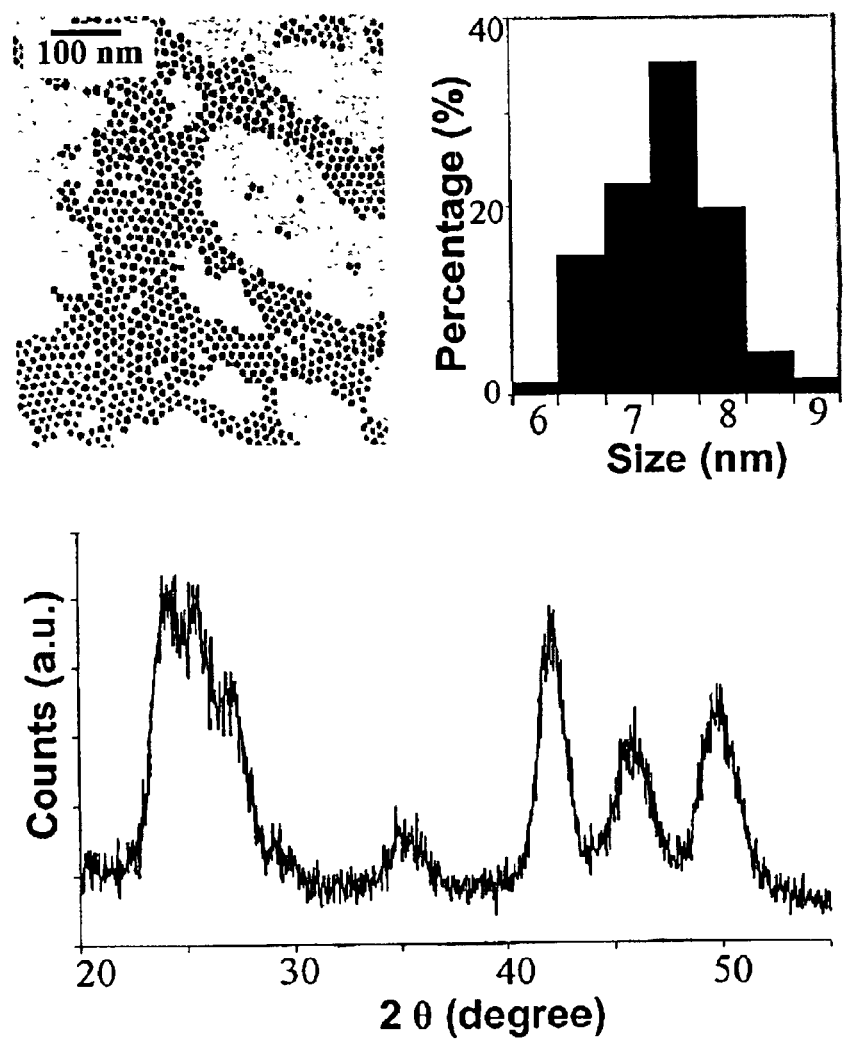
FIG. 6 presents a transmission electron microscope (TEM) image of a sample of CdSe nanocrystals (top left panel), the corresponding size-distribution histograms (top right panel), and the X-ray diffraction pattern (bottom panel) of the same sample. The crystalline domain calculated from the Debye-Sherrer equation is very close to the average size obtained from the statistics of the TEM image.

FIG. 6 presents a transmission electron microscopy (TEM) image of a sample of CdSe nanocrystals prepared according to this invention, along with the corresponding size distribution histograms, and the X-ray diffraction pattern of the same sample. We note that the crystalline domain calculated from the Debye-Sherrer equation is very close to the average size obtained from the statistics of the TEM image. As confirmed by transmission electron microscopy (TEM) (FIG. 6, top left panel), the nanocrystals synthesized by the current synthetic approach were dot shaped. The size distribution, also determined by TEM, was found to have a standard deviation of typically around 5–10%.

The crystal structure of the resulting nanocrystals was found to be quite sensitive to both the reaction temperature and the chain length of the amines. Primary amines were found as a important ingredient in the current system for growing nanocrystals with a high PL efficiency. For the nanoparticle crystallizations that occurred below about 230° C. and in a solvent containing dodecylamine (DDA, $C_{12}H_{25}NH_2$), the XRD patterns of the resulting CdSe nanocrystals were very much like that of zinc blende CdSe. At high temperatures, above about 270° C., in a solvent containing octadecylamine (ODA, $C_{18}H_{37}NH_2$), nanocrystals formed which exhibited diffraction patterns similar to almost perfect wurtzite CdSe nanocrystals. (Qu, L.; Peng, Z. A.; Peng, X. Nano Lett. 2001, 1, 333) At temperatures between about 250° C. and about 320° C. and in a solvent containing hexadecylamine (HDA, $C_{16}H_{33}NH_2$), synthesis always produced CdSe nanocrystals with the wurtzite structure, with 1–2 stacking faults perpendicular to the (001) axis (a typical pattern in FIG. 6, bottom panel), (Murray, C. B.; Norris, D. J.; Bawendi, M. G. J. Am. Chem. Soc. 1993, 115, 8706–8715) regardless of the initial Cd:Se ratio of the precursors in the solution. Unless otherwise specified, the results presented herein are all related to the reactions carried out at between about 270–320° C. in a solvent containing HDA.

The Cd:Se atomic ratio of the resulting CdSe nanocrystals was determined to be close to 1:1 within experimental error by X-ray photoelectron spectroscopy, despite the large difference in the initial Cd:Se ratio of the precursors in the reaction solutions. This indicates that the composition of the CdSe nanocrystals synthesized under different conditions mentioned above was not seriously distorted, which is similar to the results observed in molecular beam epitaxy (MBE) structures.

Amine Selection for Controlling Nanocrystal Properties

As disclosed above, primary amines were important ingredients in the current system for growing nanocrystals with a high PL efficiency (PL QY). Among all three primary amines tested, DDA provided nanocrystals exhibiting the lowest PL QY values, probably because the reaction temperatures of the related synthesis were limited below about 230° C. The ODA reactions yielded nanocrystals with a nearly perfect wurtzite structure and a moderately high PL QY at the bright points (PL QY of 50–60% with a large excess of the selenium precursor). The amine HDA was found to be the best primary amine in terms of generating the nanocrystals with a high PL QY. As a secondary amine, the presence of dioctylamine (DOA, $(C_8H_{17})_2NH$) had only a minimal effect on the emission properties of the resulting CdSe nanocrystals, regardless of whether DOA was originally in the hot cadmium solution or in the cold selenium solution. However, because DOA is much less toxic than tributylphosphine (TBP, $P(C_4H_9)_3$), most experiments were performed with DOA as the solvent of the selenium precursor (Se-TBP), instead of pure TBP.

Theoretical Considerations Regarding the Photoluminescence (PL) Bright Point and Focusing Point of Size Distribution The existence and evolution of the PL bright point, as disclosed herein, can explain why the PL properties of as-prepared semiconductor nanocrystals using conventional methods are often unpredictable and non-reproducible. In a traditional synthesis, the initial Cd:Se precursor ratio was close to unity, which can result in a sharp bright point as shown in FIG. 3. However, a time difference of only tens of seconds can vary the PL QY by several times, irrespective of the relatively unchanged average size and size distribution of the sample within the same time period. Previously, semiconductor nanocrystal synthesis has generally not been monitored for changes in nanocrystal properties over time, or simply monitored by the absorption measurements, which at best provided only size and size distribution information on the nanocrystals in solution. The results described herein indicate that tailoring the PL properties of as-prepared semiconductor nanocrystals requires the identification of the PL bright point for the adopted synthetic scheme prior to any practical synthesis, and monitoring PL QY closely during nanocrystal growth.

The origin of the PL bright point during the growth of the nanocrystals cannot yet be unambiguously determined. While not intending to be bound by the following statements, it is believed that the PL bright point relates to changes in surface structure of the nanocrystals, including surface passivation changes, as follows. In general, a low PL QY is considered a result of the surface states located in the band gap of the nanocrystals, which act as trapping states for the photogenerated charges. These surface trapping states are believed to originate from the dangling bonds of some of the surface atoms of the nanocrystals, that is, surface atom orbitals directed into solution. (See For example, Fu, H.; Zunger, A. Phys. Rev. B: Condens. Matter 1997, 56, 1496–1508.) Ligands associated with the surface of the nanocrystal may remove some or all of the surface trapping states and increase the PL QY. Theoretical treatments indicate that the efficiency of the electronic passivation provided by the surface ligands depends strongly on the surface structure and the nature of the surface states of the nanocrystals themselves. (For example, Fu, H.; Zunger, A. Phys. Rev. B: Condens. Matter 1997, 56, 1496–1508) If the surface ligands could provide a good electronic passivation for the surface states of the nanocrystals, a high PL QY should be expected. By comparing the PL QY of the nanocrystals coated by different amine ligands, one could conclude that the ligands' passivation should have played a vital role in the high PL QY of the resulting CdSe nanocrystals. However, it is difficult for surface passivation alone to explain the existence of the PL bright point, the temporal evolution pattern of the PL properties, or the relationship between the PL QY at the bright point and the Cd:Se ratio of the initial precursors in solution. For example, the reactions illustrated in FIGS. 3 and 4 were all performed with a nearly identical concentration of HDA (hexadecylamine), specifically about 2 g of HDA in the hot cadmium solution before the injection. Thus, it is difficult to understand how the surface passivation of the nanocrystals in the solution varied so much in such a short time, and resulted in the PL QY increasing several times to attain a maximum, and then decreasing to a fraction of that maximum value.

The nature and density of the surface trapping states should strongly depend on the surface structure of the nanocrystals. Furthermore, the atomic configuration of the surface of a nanocrystal should significantly affect the efficiency of the electronic passivation provided by the surface ligands. The latter effect can be visualized by simply considering the steric effect of the surface configuration of the nanocrystals on the packing of the surface ligands. For these two reasons, the surface structure of the CdSe nanocrystals themselves should play an important role in determining the PL properties of the nanocrystals. Therefore, it may be possible that the PL bright point is a signature of an optimal surface structure/reconstruction of the CdSe nanocrystals grown under certain conditions, which minimizes the surface states located in the band gap of the resulting nanocrystals. Hess, B. C.; Okhrimenko, I. G.; Davis, R. C.; Stevens, B. C.; Schulzke, Q. A.; Wright, K. C.; Bass, C. D.; Evans, C. D.; Summers, S. L. *Phys. Rev. Lett.* 2001, 86, 3132–3135) It is difficult to experimentally examine the surface structure of colloidal nanocrystals at present, (Hamad, K. S.; Roth, R.; Rockenberger, J.; van Buuren, T.; Alivisatos, A. P. *Phys. Rev. Lett.* 1999, 83, 3474–3477) and theoretical studies may be required to clarify this issue. (For example, Fu, H.; Zunger, A. *Phys. Rev. B: Condens. Matter* 1997, 56, 1496–1508)

While not intending to be bound by the following statements, it is believed that the most favorable surface structure or surface reconstruction resulting from a reaction with a defined number of monomeric units is likely to be stable only for a short period of time, due to the rapid variation of both the monomer concentrations in solution. Around the focusing point of the size distribution, (Peng, X. G.; Wickham, J.; Alivisatos, A. P. *J. Am. Chem. Soc.* 1998, 120, 5343–5344) monomers on nanocrystal surfaces should be at equilibrium with monomers in the solution, thereby providing a relatively suitable environment to reach an optimal surface structure/reconstruction. This likely effect should explain why the bright point and the focusing point are somewhat close, though typically are not overlapping. When a growth reaction is far removed from the focusing point, the monomers have a strong tendency to either add to the surface of the nanocrystals at the early stages of the reaction, or to permanently leave the surface of the nanocrystals in the defocusing region, at later stages of the reaction. (Peng, X. G.; Wickham, J.; Alivisatos, A. P. *J. Am. Chem. Soc.* 1998, 120, 5343–5344) The "overdriving" of the monomers in either mode will interrupt the process of the system reaching an optimal surface structure/reconstruction. The farther removed from the focusing window the more the reaction is overdriven, and hence, the lower the quality the surface structure/reconstruction is expected to be.

If one precursor was initially in large excess, the concentration of that monomer in the solution may be considered relatively constant after the growth reaction proceeds for a short period of time. This approximate "steady state" concentration would provide a desirable condition for constructing the most favorable surface structure/reconstruction for nanocrystals. Consequently, the PL QY might attain the desired, higher level. Such an effect would explain why the PL QY at the bright point increased as the initial Cd:Se ratio of the precursors departed from 1:1. Furthermore, it is also consistent with the appearance of a relatively flat bright point at highly biased Cd:Se ratios (for example, 1:5 and 1:10) and a relatively sharp bright point when the ratio approached 1, as seen in FIG. 3. This optimal surface structure/reconstruction argument also appears consistent with the good stability of the optical properties of the CdSe nanocrystals because a more stable surface should be more inert to possible chemical and structural changes.

The temporal evolution of the PL FWHM is associated with the progression of the size distribution of the nanocrystals. Since the PL QY and the intrinsic FWHM of the nanocrystals in a solution may vary from one size to another, there is no trivial way to faithfully extract the exact size distribution from the PL spectrum of a given sample. However, it is possible to approximate the size distribution of an ensemble of nanocrystals using the PL FWHM of the sample. Using certain assumptions and algorithms suggested by Peng et al., (Peng, X. G.; Wickham, J.; Alivisatos, A. P. *J. Am. Chem. Soc.* 1998, 120, 5343–5344), a simple mathematic treatment indicates that the standard deviation in relative size of a sample is determined by the PL FWHM expressed as a wavelength, and is independent of the emission peak position or the average size of the nanocrystals. Therefore, the PL FWHM wavelength evolution pattern can be approximately interpreted as the temporal evolution of the size distribution of the nanocrystals. This result implies that the PL bright point and the focusing point of size distribution for the same reaction do not always overlap though they may appear quite close to each other (see FIGS. 2–4).

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

EXAMPLE 1
General Synthetic and Experimental Details

The compounds trioctylphosphine oxide (TOPO), tributylphosphine (TBP), hexadecylamine, octadecylamine, stearic acid, CdO, and Se powder were purchased from Aldrich Chemical Company (Milwaukee, Wis.). Methanol, toluene, dodecylamine, chloroform, and acetone were purchased from VWR Scientific. Unless specified otherwise, the synthetic and characterization methods of nanocrystals used were similar to the ones reported previously for CdSe. (See: Peng, Z. A.; Peng, X. G. *J. Am. Chem. Soc.* 2001, 123, 1389–1395; Peng, Z. A.; Peng, X. *J. Am. Chem. Soc.* 2001, 123, 183–184; and Qu, L.; Peng, Z. A.; Peng, X. *Nano Lett.* 2001, 1, 333.)

EXAMPLE 2
Preparation of CdSe Nanocrystals with High Photoluminescence (PL) Efficiency A typical synthesis of CdSe nanocrystals which exhibit a high photoluminescence (PL) efficiency is carried out as follows. A 0.0127 g (0.1 mmol) sample of CdO and 0.1140 g (0.4 mmol) of stearic acid were loaded into a 25 mL three-neck flask and heated to 150° C. under an argon flow. After the CdO was completely dissolved, the mixture was allowed to cool to room temperature, after which trioctylphosphine oxide (TOPO) and hexadecylamine (HDA), 1.94 g of each, were added to the flask. This mixture was stirred and heated to 320° C. under an argon flow to form an optically clear solution. At this temperature, the Se solution containing 0.079 g (1 mmol) of elemental Se dissolved in 0.238 g (1.18 mmol) of tributylphosphine (TBP) and 1.681 g of dioctylamine was swiftly injected into the reaction flask. After injection, the temperature was maintained at 290° C. for growth of the nanocrystals. At various time intervals, aliquots of a needle-tip amount of the reaction mixture were removed and diluted with chloroform. Insoluble white solid, if it existed, was separated by centrifugation and decantation prior to any further measurements. The UV-vis spectrum and the photoluminescence (PL) spectrum of the aliquots were recorded promptly (see FIG. 1). A Jeol 100 CX transmission electron microscope was used for measuring the size and size distribution of the resulting nanocrystals by depositing them on carbon-coated copper grids. The powder X-ray diffraction (XRD) patterns were employed to check the crystallinity of the final products after extensive purification to remove excess ligands and reaction precursors, as described below. The reaction mixture of a reaction was mixed with about 15 mL of chloroform after the reaction mixture was allowed to cool to 30–50° C. and was not completely solidified. The nanocrystal solution was separated from any insoluble white or reddish solid floating on the top of the chloroform solution by centrifugation and decantation. The nanocrystals were precipitated by adding methanol or acetone to the chloroform solution and isolated by centrifugation and decantation. The resulting wet precipitate was stored for future use. For the XRD and X-ray photoelectron spectroscopy measurements, the wet precipitate was dissolved in chloroform and then precipitated from the chloroform solution by adding methanol or acetone. This precipitate was isolated by centrifugation and decantation. This cycle of the dissolution, precipitation, centrifugation, and decantation was repeated at least three times prior to the measurements.

EXAMPLE 3
Photoluminescence Quantum Yield Measurements of CdSe Nanocrystals

The photoluminescence (PL) spectra of a given sample of the CdSe nanocrystals and an organic dye, whose PL spectrum overlaps significantly with that of the nanocrystal sample, were measured under the same setting of a Hitachi 2500 spectrophotometer. The scanning step of the spectrophotometer was set as 1 nm and marked as the error bars in the related figures. The optical density (OD) at the excitation wavelength of the dye and the nanocrystal sample was set to a similar value. The OD at either the first exciton absorption peak of the nanocrystals or the main absorption peak of the dye was below 0.1 in order to avoid any significant reabsorption. The PL quantum yield (QY) of the nanocrystal sample was finally obtained by comparing the integrated PL intensities of the nanocrystals with the corresponding dye. The measurement error of the PL QY was estimated to be about 5% and reported in the related figures as the error bars. The PL QY values of the following dyes in Table 1 were provided by the dye vendor (Exciton).

TABLE 1

The photoluminescence quantum yield (PL QY) values of selected dyes.

| Dye | Coumarin | R6G | R3B | R640 | LD690 |
| --- | --- | --- | --- | --- | --- |
| Absorption (nm) | 458 | 528 | 550 | 570 | 616 |
| PL QY (%) | 62 | 95 | 50 | 100 | 63 |

EXAMPLE 4
Preparation of CdTe Nanocrystals with High Photoluminescence (PL) Efficiency The synthesis of CdTe nanocrystals could be carried out using an excess of either the anion or cation precursor, in a similar fashion as described in Example 2, to provide nanocrystal samples exhibiting a high PL QY.

EXAMPLE 5
Preparation of ZnSe Nanocrystals with High Photoluminescence (PL) Efficiency The synthesis of ZnSe nanocrystals could be carried out using an excess of either the anion or cation precursor, in a similar fashion as described in Example 2, to provide nanocrystal samples exhibiting a high PL QY.

EXAMPLE 6
Preparation of ZnTe Nanocrystals with High Photoluminescence (PL) Efficiency The synthesis of ZnTe nanocrystals could be carried out using an excess of either the anion or cation precursor, in a similar fashion as described in Example 2, to provide nanocrystal samples exhibiting a high PL QY.

EXAMPLE 7
Preparation of CdS Nanocrystals with High Photoluminescence (PL) Efficiency The synthesis of CdS nanocrystals could be carried out using an excess of either the anion or cation precursor, in a similar fashion as described in Example 2, to provide nanocrystal samples exhibiting a high PL QY.

EXAMPLE 8
Preparation of ZnS Nanocrystals with High Photoluminescence (PL) Efficiency The synthesis of ZnS nanocrystals could be carried out using an excess of either the anion or cation precursor, in a similar fashion as described in Example 2, to provide nanocrystal samples exhibiting a high PL QY.

All of the publications or patents mentioned herein are hereby incorporated by reference in their entireties. The above examples are merely demonstrative of the present invention, and are not intended to limit the scope of the appended claims.

What is claimed is:

1. A composition comprising colloidal nanocrystals, prepared by the method comprising:
   a) combining a cation precursor, a first ligand, and a first solvent to form a cation-ligand complex;
   b) admixing an anion precursor with the cation-ligand complex at a first temperature sufficient to induce reaction therebetween, wherein the initial concentration of the anion precursor is about 10 times the initial concentration of the cation precursor in the mixture; and
   c) adjusting the temperature of the mixture to a second temperature sufficient to form nanocrystals of the reaction product;
   wherein the nanocrystals do not comprise tellurides.

2. A light emitting diode comprising the composition of claim 1.

3. A biological labeling agent comprising the composition of claim 1.

4. A photoelectric device comprising the composition of claim 1.

5. A solar cell comprising the composition of claim 1.

6. A catalyst comprising the composition of claim 1.

7. A method of synthesizing colloidal nanocrystals with an improved photoluminescence quantum yield, comprising:
   a) combining a cation precursor, a first ligand, and a first solvent to form a cation-ligand complex;
   b) admixing an anion precursor with the cation-ligand complex at a first temperature sufficient to induce reaction therebetween, wherein the initial concentration of the anion precursor is about 10 times the initial concentration of the cation precursor in the mixture; and c) adjusting the temperature of the mixture to a second temperature sufficient to form nanocrystals of the reaction product.

8. A method of synthesizing colloidal nanocrystals with an improved photoluminescence quantum yield, comprising:

a) combining a cation precursor, a first ligand, and a first solvent to form a cation-ligand complex;

b) admixing an anion precursor with the cation-ligand complex at a first temperature sufficient to induce reaction therebetween wherein the concentration of the anion precursor is about 20 times the concentration of the cation precursor in the mixture; and c) adjusting the temperature of the mixture to a second temperature sufficient to form nanocrystals of the reaction product.

9. The method of claim 7, wherein the cation precursor comprises a metal oxide, a metal carbonate, a metal bicarbonate, a metal sulfate, a metal sulfite, a metal phosphate, a metal phosphite, a metal halide, a metal carboxylate, a metal alkoxide, a metal thiolate, a metal amide, a metal imide, a metal alkyl, a metal aryl, a metal coordination complex, a metal solvate, or a metal salt.

10. The method of claim 7, wherein the cation precursor comprises a compound of a group II metal, a group III metal, a group IV metal, or a transition metal.

11. The method of claim 7, wherein the cation precursor comprises a compound of Cd or Zn.

12. The method of claim 7, wherein the first ligand is selected from a fatty acid, a phosphine, a phosphine oxide, a phosphonic acid, an amine-containing dendron, or a combination thereof.

13. The method of claim 7, wherein the first ligand is selected from oleic acid, decanoic acid, lauric acid, myristic acid, palmitic acid, stearic acid, or a combination thereof.

14. The method of claim 7, wherein the first solvent comprises a primary amine.

15. The method of claim 7, wherein the first solvent is selected from dodecylamine, hexadecylamine, octadecylamine, dioctylamine, or a combination thereof.

16. The method of claim 7, wherein the anion precursor is combined with a second ligand, a second solvent, or a combination thereof, prior to admixing with the cation-ligand complex.

17. The method of claim 16, wherein the cation precursor is CdO, the first ligand is stearic acid, the first solvent is hexadecylamine, the anion precursor is elemental selenium, and the second ligand is tributylphosphine.

18. The method of claim 7, wherein the anion precursor is selected from an element, a covalent compound, or an ionic compound.

19. The method of claim 7, wherein the anion precursor is selected from elemental S, elemental Se, elemental Te, selenium tributylphosphine, or tellurium tributylphosphine.

20. The method of claim 7, wherein the second temperature is from about 250° C. to about 320° C.

21. The method of claim 7, wherein the photoluminescence emission peak of the colloidal nanocrystals occurs from about 500 nm to about 680 nm.

22. The method of claim 7, wherein the cation precursor is CdO, the first ligand is stearic acid, the first solvent comprises dodecylamine, the anion precursor is elemental selenium, the second temperature is below about 230° C., and the reaction product comprises zinc blende CdSe nanocrystals.

23. The method of claim 7, wherein the cation precursor is CdO, the first ligand is stearic acid, the first solvent comprises octadecylamine, the anion precursor is elemental selenium, the second temperature is above about 270° C., and the reaction product comprises wurtzite CdSe nanocrystals.

24. The method of claim 7, wherein the cation precursor is CdO, the first ligand is stearic acid, the first solvent comprises hexadecylamine, the anion precursor is elemental selenium, the second temperature is from about 250° C. to about 320° C., and the reaction product comprises wurtzite CdSe nanocrystals with stacking faults perpendicular to the (001) axis.

* * * * *